United States Patent
Rappuoli et al.

(10) Patent No.: US 8,697,087 B2
(45) Date of Patent: Apr. 15, 2014

(54) INFLUENZA VACCINES INCLUDING COMBINATIONS OF PARTICULATE ADJUVANTS AND IMMUNOPOTENTIATORS

(75) Inventors: Rino Rappuoli, Siena (IT); Derek O'Hagan, Siena (IT); Giuseppe Del Giudice, Siena (IT)

(73) Assignee: Novartis AG, Basel (CH)

( * ) Notice: Subject to any disclaimer, the term of this patent is extended or adjusted under 35 U.S.C. 154(b) by 437 days.

(21) Appl. No.: 12/092,162

(22) PCT Filed: Nov. 6, 2006

(86) PCT No.: PCT/GB2006/004133
§ 371 (c)(1), (2), (4) Date: Sep. 26, 2008

(87) PCT Pub. No.: WO2007/052058
PCT Pub. Date: May 10, 2007

(65) Prior Publication Data
US 2009/0304739 A1    Dec. 10, 2009

Related U.S. Application Data

(60) Provisional application No. 60/734,026, filed on Nov. 4, 2005, provisional application No. 60/735,468, filed on Nov. 11, 2005.

(51) Int. Cl.
*A61K 39/39* (2006.01)
*C12N 1/20* (2006.01)

(52) U.S. Cl.
USPC ...................................... 424/209.1; 536/24.1

(58) Field of Classification Search
None
See application file for complete search history.

(56) References Cited

U.S. PATENT DOCUMENTS

| | | | |
|---|---|---|---|
| 7,384,642 B2 * | 6/2008 | Minke et al. | 424/210.1 |
| 7,425,336 B2 * | 9/2008 | Minke et al. | 424/209.1 |
| 2007/0048821 A1 * | 3/2007 | Minke et al. | 435/69.1 |

FOREIGN PATENT DOCUMENTS

| | | | |
|---|---|---|---|
| JP | 62201573 | | 9/1987 |
| WO | WO 98/16247 | * | 4/1998 |
| WO | WO 98/40100 | | 9/1998 |
| WO | WO 99/27961 | | 6/1999 |
| WO | WO-00/15251 | | 3/2000 |
| WO | WO 2004/084937 | | 10/2004 |

OTHER PUBLICATIONS

Galarza et al. Viral Immunology, 2005, vol. 18, No. 2, pp. 365-372.*
Joseph et al. Vaccine 2002, vol. 20, pp. 3342-3354.*
Fukuda et al. Inactivated influenza Vaccines in Chapter 17, 2004, pp. 339-370.*
Krieg et al. Nature Medicine 2003, vol. 9, pp. 831-835.*
Chattaraj et al., "Biodegradable microparticles of influenza viral vaccine: comparison of the effects of routes of administration on the in vivo immune response in mice," *J. Controlled Release* 58, 223-32, Mar. 29, 1999.
Cooper et al., "Safety and immunogenicity of CPG 7909 injection as an adjuvant to Fluarix influenza vaccine," *Vaccine* 22, 3136-43, Aug. 13, 2004.
Galarza et al., "Virus-like particle vaccine conferred complete protection against a lethal influenza virus challenge," *Viral Immunol.* 18, 365-72, Jun. 2005.
Hehme et al., "Immunogenicity of a monovalent, aluminum-adjuvanted influenza whole virus vaccine for pandemic use," *Virus Res.* 103, 163-71, Jul. 2004.
Ichinohe et al., "Synthetic double-stranded RNA poly(I:C) combined with mucosal vaccine protects against influenza virus infection," *J. Virol.* 79, 2910-19, Mar. 2005.
Joseph et al., "Liposomal immunostimulatory DNA sequence (ISS-ODN): an efficient parenteral and mucosal adjuvant for influenza and hepatitis B vaccines," *Vaccine* 20, 3342-54, Sep. 10, 2002.
Klinman, "Immunotherapeutic uses of CpG oligodeoxynucleotides," *Nat. Rev. Immunol.* 4, 249-58, Apr. 2004.
Moldoveanu et al., "CpG DNA, a novel immune enhancer for systemic and mucosal immunization with influenza virus," *Vaccine* 16, 1216-24, Jul. 1998.
O'Hagan et al., "Novel approaches to vaccine delivery," *Pharmaceutical Res.* 21, 1519-30, Sep. 2004.
Ulmer et al., "Vaccine manufacturing: challenges and solutions," *Nature Biotechnol.* 24, 1377-83, Nov. 2006.
Bordi F et al. (Dec. 2002). "Salt-induced aggregation in cationic liposome aqueous suspensions resulting in multi-step self-assembling complexes", Colloids and Surfaces B: Biointerfaces 26(4):341-350.
O'Hagan et al. (Apr. 1, 2003). "Microparticles as vaccine adjuvants and delivery systems," Expert Review of Vaccines 2(2):269-283.
Singh et al. (Feb. 23, 2001) "A novel bioadhesive intranasal delivery system for inactivated influenza vaccines", Journal of Controlled Release 70(3):267-276.
Singh et al. (2001). "Cationic microparticles are an effective delivery system for immune stimulatory cpG DNA," Pharm Res. 18(10):1476-9.
Vasilakos et al. (2000). "Adjuvant activities of immune response modifier R-848: comparison with CpG ODN," Cell Immunol. Aug. 25, 2000;204(1):64-74.

* cited by examiner

*Primary Examiner* — Bao Li
(74) *Attorney, Agent, or Firm* — Helen Lee; Otis Littlefield

(57) ABSTRACT

Influenza vaccines containing insoluble particulate adjuvants have been found to elicit an IgG response that is primarily a TH2 response (IgG1). This response can be shifted towards a TH1 response (IgG2a) by including immunopotentiators in the compositions. Thus the invention provides an immunogenic composition comprising: (i) an influenza virus antigen; (ii) an insoluble particulate adjuvant; and (iii) a immunopotentiator.

14 Claims, 3 Drawing Sheets

INFLUENZA VACCINES INCLUDING COMBINATIONS OF PARTICULATE ADJUVANTS AND IMMUNOPOTENTIATORS

This application is a national stage application of PCT/GB2006/004133 filed Nov. 6, 2006, which claims the benefit of Ser. No. 60/734,026 filed Nov. 4, 2005 and Ser. No. 60/735,468 filed Nov. 11, 2005. Each of these applications is incorporated herein by reference in its entirety.

All documents cited herein are incorporated by reference in their entirety.

TECHNICAL FIELD

This invention is in the field of adjuvanted vaccines for protecting against influenza virus infection.

BACKGROUND ART

Except for FLUAD™ product (Chiron Vaccines), which uses the MF59 oil-in-water emulsion adjuvant [1], influenza vaccines currently in general use do not include an adjuvant. These vaccines are described in more detail in chapters 17 & 18 of reference 2. They are based on live virus or inactivated virus, and inactivated vaccines can be based on whole virus, 'split' virus or on purified surface antigens (including hemagglutinin and neuraminidase). Haemagglutinin (HA) is the main immunogen in inactivated influenza vaccines, and vaccine doses are standardized by reference to HA levels, with vaccines typically containing about 15 µg of HA per strain.

In a pandemic influenza outbreak then a large number of doses of influenza vaccine will be needed, but it will be difficult to increase vaccine supply to meet the huge demand. Rather than produce more vaccine antigen, therefore, it has been proposed to use a lower amount of antigen per strain, and to use an adjuvant to compensate for the reduced antigen dose. It has also been proposed to use the same approach in inter-pandemic periods e.g. to allow greater coverage of the population without increasing manufacturing levels.

Insoluble particulate adjuvants [3], such as aluminum salts [4-7] or microparticles [8], have been suggested for improving influenza vaccines. While these adjuvanted vaccines are useful, there remains scope for improvement. Thus it is an object of the invention to provide further and improved adjuvanted influenza vaccines (for both pandemic and interpandemic use) and methods for their preparation.

DISCLOSURE OF THE INVENTION

Influenza vaccines containing insoluble particulate adjuvants have been found to elicit an IgG response that is primarily a TH2 response (IgG1). This response can be shifted towards a TH1 response (IgG2a) by including immunopotentiators in the compositions. TH1-type responses [9] have been reported to improve heterosubtypic immunity against influenza virus. Advantageously, the immunopotentiators have also been found increase haemagglutination titers and anti-haemagglutinin ELISA titers.

Therefore the invention provides an immunogenic composition comprising: (i) an influenza virus antigen; (ii) an insoluble particulate adjuvant; and (iii) an immunopotentiator.

The invention also provides a method for preparing an immunogenic composition comprising the steps of combining: (i) an influenza virus antigen; (ii) an insoluble particulate adjuvant; and (iii) an immunopotentiator.

The invention provides a kit comprising: (i) a first kit component comprising an influenza virus antigen; and (ii) a second kit component comprising an insoluble particulate adjuvant, wherein either (a) the first component or the second component includes an immunopotentiator, or (b) the kit includes a third kit component comprising an immunopotentiator.

The Influenza Virus Antigen

Compositions of the invention include an influenza virus antigen. The antigen will typically be prepared from influenza virions but, as an alternative, antigens such as haemagglutinin can be expressed in a recombinant host (e.g. in an insect cell line using a baculovirus vector) and used in purified form [10,11]. In general, however, antigens will be from virions.

The antigen may take the form of a live virus or, more preferably, an inactivated virus. Chemical means for inactivating a virus include treatment with an effective amount of one or more of the following agents: detergents, formaldehyde, formalin, β-propiolactone, or UV light. Additional chemical means for inactivation include treatment with methylene blue, psoralen, carboxyfullerene (C60) or a combination of any thereof. Other methods of viral inactivation are known in the art, such as for example binary ethylamine, acetyl ethyleneimine, or gamma irradiation. The INFLEXAL™ product is a whole virion inactivated vaccine.

Where an inactivated virus is used, the vaccine may comprise whole virion, split virion, or purified surface antigens (including hemagglutinin and, usually, also including neuraminidase).

Virions can be harvested from virus-containing fluids by various methods. For example, a purification process may involve zonal centrifugation using a linear sucrose gradient solution that includes detergent to disrupt the virions. Antigens may then be purified, after optional dilution, by diafiltration.

Split virions are obtained by treating virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses are well known in the art e.g. see refs. 12-17, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as $CaHPO_4$ adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. The BEGRIVAC™, FLUARIX™, FLUZONE™ and FLUSHIELD™ products are split vaccines.

Purified surface antigen vaccines comprise the influenza surface antigens haemagglutinin and, typically, also neuraminidase. Processes for preparing these proteins in purified form are well known in the art. The FLUVIRIN™, AGRIPPAL™ and INFLUVAC™ products are subunit vaccines.

Influenza antigens can also be presented in the form of virosomes [18].

The influenza virus may be attenuated. The influenza virus may be temperature-sensitive. The influenza virus may be cold-adapted. These three possibilities apply in particular for live viruses.

Influenza virus strains for use in vaccines change from season to season. In the current inter-pandemic period, vaccines typically include two influenza A strains (H1N1 and H3N2) and one influenza B strain, and trivalent vaccines are typical. The invention may also use viruses from pandemic strains (i.e. strains to which the vaccine recipient and the general human population are immunologically naïve), such as H2, H5, H7 or H9 subtype strains (in particular of influenza A virus), and influenza vaccines for pandemic strains may be monovalent or may be based on a normal trivalent vaccine supplemented by a pandemic strain. Depending on the season and on the nature of the antigen included in the vaccine, however, the invention may protect against one or more of influenza A virus hemagglutinin subtypes H1, H2, H3, H4, H5 H6, H7, H8, H9, H10, H11, H12, H13, H14, H15 or H16. The invention may protect against one or more of influenza A virus NA subtypes N1, N2, N3, N4, N5, N6, N7, N8 or N9.

Other strains that can usefully be included in the compositions are strains which are resistant to antiviral therapy (e.g. resistant to oseltamivir [19] and/or zanamivir), including resistant pandemic strains [20].

The adjuvanted compositions of the invention are particularly useful for immunizing against pandemic strains. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. A virus with H5 haemagglutinin type is preferred for immunising against pandemic influenza, such as a H5N1 strain. Other possible strains include H5N3, H9N2, H2N2, H7N1 and H7N7, and any other emerging potentially pandemic strains. Within the H5 subtype, a virus may fall into HA clade 1, HA clade 1', HA clade 2 or HA clade 3 [21], with clades 1 and 3 being particularly relevant.

Compositions of the invention may include antigen(s) from one or more (e.g. 1, 2, 3, 4 or more) influenza virus strains, including influenza A virus and/or influenza B virus. Where a vaccine includes more than one strain of influenza, the different strains are typically grown separately and are mixed after the viruses have been harvested and antigens have been prepared. Thus a process of the invention may include the step of mixing antigens from more than one influenza strain.

The influenza virus may be a reassortant strain, and may have been obtained by reverse genetics techniques. Reverse genetics techniques [e.g. 22-26] allow influenza viruses with desired genome segments to be prepared in vitro using plasmids. Typically, it involves expressing (a) DNA molecules that encode desired viral RNA molecules e.g. from polI promoters, and (b) DNA molecules that encode viral proteins e.g. from polII promoters, such that expression of both types of DNA in a cell leads to assembly of a complete intact infectious virion. The DNA preferably provides all of the viral RNA and proteins, but it is also possible to use a helper virus to provide some of the RNA and proteins. Plasmid-based methods using separate plasmids for producing each viral RNA are preferred [27-29], and these methods will also involve the use of plasmids to express all or some (e.g. just the PB1, PB2, PA and NP proteins) of the viral proteins, with 12 plasmids being used in some methods.

To reduce the number of plasmids needed, a recent approach [30] combines a plurality of RNA polymerase I transcription cassettes (for viral RNA synthesis) on the same plasmid (e.g. sequences encoding 1, 2, 3, 4, 5, 6, 7 or all 8 influenza A vRNA segments), and a plurality of protein-coding regions with RNA polymerase II promoters on another plasmid (e.g. sequences encoding 1, 2, 3, 4, 5, 6, 7 or all 8 influenza A mRNA transcripts). Preferred aspects of the reference 30 method involve: (a) PB1, PB2 and PA mRNA-encoding regions on a single plasmid; and (b) all 8 vRNA-encoding segments on a single plasmid. Including the NA and HA segments on one plasmid and the six other segments on another plasmid can also facilitate matters.

As an alternative to using polI promoters to encode the viral RNA segments, it is possible to use bacteriophage polymerase promoters [31]. For instance, promoters for the SP6, T3 or T7 polymerases can conveniently be used. Because of the species-specificity of polI promoters, bacteriophage polymerase promoters can be more convenient for many cell types (e.g. MDCK), although a cell must also be transfected with a plasmid encoding the exogenous polymerase enzyme.

In other techniques it is possible to use dual polI and polII promoters to simultaneously code for the viral RNAs and for expressible mRNAs from a single template [32,33].

Thus an influenza A virus may include one or more RNA segments from a A/PR/8/34 virus (typically 6 segments from A/PR/8/34, with the HA and N segments being from a vaccine strain, i.e. a 6:2 reassortant), particularly when viruses are grown in eggs. It may also include one or more RNA segments from a A/WSN/33 virus, or from any other virus strain useful for generating reassortant viruses for vaccine preparation. Typically, the invention protects against a strain that is capable of human-to-human transmission, and so the strain's genome will usually include at least one RNA segment that originated in a mammalian (e.g. in a human) influenza virus.

It may include NS segment that originated in an avian influenza virus.

The viruses used as the source of the antigens can be grown either on eggs (usually SPF eggs) or on cell culture. The current standard method for influenza virus growth uses embryonated hen eggs, with virus being purified from the egg contents (allantoic fluid). More recently, however, viruses have been grown in animal cell culture and, for reasons of speed and patient allergies, this growth method is preferred. If egg-based viral growth is used then one or more amino acids may be introduced into the allantoid fluid of the egg together with the virus [15].

The cell substrate will typically be a mammalian cell line. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line. Suitable dog cells are e.g. kidney cells, as in the MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [34-37], derived from Madin Darby canine kidney; Vero cells [38-40], derived from African green monkey (*Cercopithecus aethiops*) kidney; or PER.C6 cells [41], derived from human embryonic retinoblasts. These cell lines are widely available e.g. from the American Type Cell Culture (ATCC) collection [42], from the Coriell Cell Repositories [43], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 44-46], including cell lines derived from ducks (e.g. duck retina) or hens e.g. chicken embryo fibroblasts (CEF), etc. Examples include avian embryonic stem cells [44,47], including the EBx cell line derived from chicken embryonic stem cells, EB45, EB14, and EB14-074 [48].

Where virus has been grown on a mammalian cell line then the composition will advantageously be free from egg proteins (e.g. ovalbumin and ovomucoid) and from chicken DNA, thereby reducing allergenicity.

The most preferred cell lines for growing influenza viruses are MDCK cell lines. The original MDCK cell line is available from the ATCC as CCL-34, but derivatives of this cell line may also be used. For instance, reference 34 discloses a MDCK cell line that was adapted for growth in suspension culture ('MDCK 33016', deposited as DSM ACC 2219). Similarly, reference 49 discloses a MDCK-derived cell line that grows in suspension in serum-free culture ('B-702', deposited as FERM BP-7449). Reference 50 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 51 discloses MDCK cell lines with high susceptibility to infection, including 'MDCK.5F1' cells (ATCC CRL-12042). Any of these MDCK cell lines can be used.

Where virus has been grown on a cell line then the culture for growth, and also the viral inoculum used to start the culture, will preferably be free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [52]. Absence of herpes simplex viruses is particularly preferred.

Where virus has been grown on a cell line then the composition preferably contains less than 10 ng (preferably less than 1 ng, and more preferably less than 100 pg) of residual host cell DNA per dose, although trace amounts of host cell DNA may be present. In general, the host cell DNA that it is desirable to exclude from compositions of the invention is DNA that is longer than 100 bp.

Measurement of residual host cell DNA is now a routine regulatory requirement for biologicals and is within the normal capabilities of the skilled person. The assay used to measure DNA will typically be a validated assay [53,54]. The performance characteristics of a validated assay can be described in mathematical and quantifiable terms, and its possible sources of error will have been identified. The assay will generally have been tested for characteristics such as accuracy, precision, specificity. Once an assay has been calibrated (e.g. against known standard quantities of host cell DNA) and tested then quantitative DNA measurements can be routinely performed. Three principle techniques for DNA quantification can be used: hybridization methods, such as Southern blots or slot blots [55]; immunoassay methods, such as the Threshold™ System [56]; and quantitative PCR [57]. These methods are all familiar to the skilled person, although the precise characteristics of each method may depend on the host cell in question e.g. the choice of probes for hybridization, the choice of primers and/or probes for amplification, etc. The Threshold™ system from *Molecular Devices* is a quantitative assay for picogram levels of total DNA, and has been used for monitoring levels of contaminating DNA in biopharmaceuticals [56]. A typical assay involves non-sequence-specific formation of a reaction complex between a biotinylated ssDNA binding protein, a urease-conjugated anti-ssDNA antibody, and DNA. All assay components are included in the complete Total DNA Assay Kit available from the manufacturer. Various commercial manufacturers offer quantitative PCR assays for detecting residual host cell DNA e.g. AppTec™ Laboratory Services, BioReliance™, Althea Technologies, etc. A comparison of a chemiluminescent hybridisation assay and the total DNA Threshold™ system for measuring host cell DNA contamination of a human viral vaccine can be found in reference 58.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 59 & 60, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [61].

Vaccines containing <10 ng (e.g. <1 ng, <100 pg) host cell DNA per 15 μg of haemagglutinin are preferred, as are vaccines containing <10 ng (e.g. <1 ng, <100 pg) host cell DNA per 0.25 ml volume. Vaccines containing <10 ng (e.g. <1 ng, <100 pg) host cell DNA per 50 μg of haemagglutinin are more preferred, as are vaccines containing <10 ng (e.g. <1 ng, <100 pg) host cell DNA per 0.5 ml volume.

It is preferred that the average length of any residual host cell DNA is less than 500 bp e.g. less than 400 bp, less than 300 bp, less than 200 bp, less than 100 bp, etc.

For growth on a cell line, such as on MDCK cells, virus may be grown on cells in suspension [34,62,63] or in adherent culture. One suitable MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention in which there are no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [64] (e.g. 30-36° C., or at about 30° C., 31° C., 32° C., 33° C., 34° C., 35° C., 36° C.), for example during viral replication.

The method for propagating virus in cultured cells generally includes the steps of inoculating the cultured cells with the strain to be cultured, cultivating the infected cells for a desired time period for virus propagation, such as for example as determined by virus titer or antigen expression (e.g. between 24 and 168 hours after inoculation) and collecting the propagated virus. The cultured cells are inoculated with a virus (measured by PFU or $TCID_{50}$) to cell ratio of 1:500 to 1:1, preferably 1:100 to 1:5, more preferably 1:50 to 1:10. The virus is added to a suspension of the cells or is applied to a monolayer of the cells, and the virus is absorbed on the cells for at least 60 minutes but usually less than 300 minutes, preferably between 90 and 240 minutes at 25° C. to 40° C., preferably 28° C. to 37° C. The infected cell culture (e.g. monolayers) may be removed either by freeze-thawing or by enzymatic action to increase the viral content of the harvested culture supernatants. The harvested fluids are then either inactivated or stored frozen. Cultured cells may be infected at a multiplicity of infection ("m.o.i.") of about 0.0001 to 10, preferably 0.002 to 5, more preferably to 0.001 to 2. Still more preferably, the cells are infected at a m.o.i of about 0.01. Infected cells may be harvested 30 to 60 hours post infection. Preferably, the cells are harvested 34 to 48 hours post infection. Still more preferably, the cells are harvested 38 to 40 hours post infection. Proteases (typically trypsin) are generally added during cell culture to allow viral release, and the proteases can be added at any suitable stage during the culture.

Haemagglutinin (HA) is the main immunogen in inactivated influenza vaccines, and vaccine doses are standardised by reference to HA levels, typically as measured by a single radial immunodiffusion (SRID) assay. Vaccines typically contain about 15 μg of HA per strain, although lower doses are also used e.g. for children, or in pandemic situations. Fractional doses such as ½ (i.e. 7.5 μg HA per strain), ¼ and ⅛ have been used [6,7], as have higher doses (e.g. 3× or 9× doses [65,66]). Thus vaccines may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 1.9, about 1.5, etc. These lower doses are most useful when an adjuvant is present in the vaccine, as with the invention.

For live vaccines, dosing is measured by median tissue culture infectious dose ($TCID_{50}$) rather than HA content, and a $TCID_{50}$ of between $10^6$ and $10^8$ (preferably between $10^{6.5}$-$10^{7.5}$) per strain is typical.

HA used with the invention may be a natural HA as found in a virus, or may have been modified. For instance, it is known to modify HA to remove determinants (e.g. hyperbasic regions around the cleavage site between HA1 and HA2) that cause a virus to be highly pathogenic in avian species, as these determinants can otherwise prevent a virus from being grown in eggs.

The antigen component of the kits of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAB'), or sodium deoxycholate, particularly for a split or surface antigen vaccine. The detergent may be present only at trace amounts. Thus the vaccine may included less than 1 mg/ml of each of octoxynol-10, α-tocopheryl hydrogen succinate and polysorbate 80. Other residual components in trace amounts could be antibiotics (e.g. neomycin, kanamycin, polymyxin B).

An inactivated but non-whole cell vaccine (e.g. a split virus vaccine or a purified surface antigen vaccine) may include matrix protein, in order to benefit from the additional T cell epitopes that are located within this antigen. Thus a non-whole cell vaccine (particularly a split vaccine) that includes haemagglutinin and neuraminidase may additionally include M1 and/or M2 matrix protein. Where a matrix protein is present, inclusion of detectable levels of M2 matrix protein is preferred. Nucleoprotein may also be present.

The Insoluble Particulate Adjuvant

The compositions and kits of the invention include insoluble particulate adjuvants. Examples of suitable insoluble particulate adjuvants useful with the invention include, but are not limited to, aluminum salts, calcium salts, and microparticles.

The insoluble particulate adjuvant will typically function as an adsorbent such that, when antigen and adjuvant are mixed, the antigen (e.g. haemagglutinin) becomes adsorbed to the adjuvant. For microparticles, however, as an alternative to adsorbing the antigen (or in addition to adsorbing the antigen) on the particle surface, it is possible to encapsulate the antigen within the interior of the particles.

Aluminum Salts

Suitable aluminum salts include the adjuvants known as aluminum hydroxide and aluminum phosphate. These names are conventional, but are used for convenience only, as neither is a precise description of the actual chemical compound which is present [e.g. see chapter 9 of reference 67]. The invention can use any of the "hydroxide" or "phosphate" adjuvants that are in general use as adjuvants.

The adjuvants known as "aluminum hydroxide" are typically aluminum oxyhydroxide salts, which are usually at least partially crystalline. Aluminum oxyhydroxide, which can be represented by the formula AlO(OH), can be distinguished from other aluminum compounds, such as aluminum hydroxide $Al(OH)_3$, by infrared (IR) spectroscopy, in particular by the presence of an adsorption band at 1070 cm$^{-1}$ and a strong shoulder at 3090-3100 cm$^{-1}$ [chapter 9 of ref. 67]. The degree of crystallinity of an aluminum hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminum hydroxide adjuvants. The pI of aluminum hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminum hydroxide adjuvants.

The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls [chapter 9 of ref. 67].

The PO$_4$/Al$^{3+}$ molar ratio of an aluminum phosphate adjuvant will generally be between 0.3 and 1.2, preferably between 0.8 and 1.2, and more preferably 0.95±0.1. The aluminum phosphate will generally be amorphous, particularly for hydroxyphosphate salts. A typical adjuvant is amorphous aluminum hydroxyphosphate with PO$_4$/Al molar ratio between 0.84 and 0.92, included at 0.6 mg Al$^{3+}$/ml. The aluminum phosphate will generally be particulate (e.g. plate-like morphology as seen in transmission electron micrographs). Typical diameters of the particles are in the range 0.5-20 µm (e.g. about 5-10 µm) after any antigen adsorption. Adsorptive capacities of between 0.7-1.5 mg protein per mg Al$^{+++}$ at pH 7.4 have been reported for aluminum phosphate adjuvants.

The point of zero charge (PZC) of aluminum phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminum phosphates used according to the invention will generally have a PZC of between 4.0 and 7.0, more preferably between 5.0 and 6.5 e.g. about 5.7.

Suspensions of aluminum salts used with the invention may contain a buffer (e.g. a phosphate or a histidine or a Tris buffer), but this is not always necessary. The suspensions are preferably sterile and pyrogen-free. A suspension may include free aqueous phosphate ions e.g. present at a concentration between 1.0 and 20 mM, preferably between 5 and 15 mM, and more preferably about 10 mM. The suspensions may also comprise sodium chloride.

In one embodiment of the invention, the adjuvant includes a mixture of both an aluminum hydroxide and an aluminum phosphate [6]. In this case there may be more aluminum phosphate than hydroxide e.g. a weight ratio of at least 2:1 e.g. ≥5:1, ≥6:1, ≥7:1, ≥8:1, ≥9:1, etc.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred.

Calcium Salts

Of the various calcium salts, in general only calcium phosphate is used as an adjuvant. Various adjuvant forms of calcium phosphate have been reported, and any of these can be used with the invention:

Hydrated calcium phosphate gel adjuvant is available from Superfos (Vedbaek, Denmark).

Chapter 8 of reference 67 reviewed calcium phosphate adjuvants in 1995. Antigens can be adsorbed to calcium phosphate either by in situ precipitation of the salt in the presence of the antigens or by adsorption to a pre-formed salt. Commercial sources of pre-formed calcium phosphate gel are mentioned. Details are given on the effect of precipitation conditions on physicochemical characteristics of the adjuvant, including adsorption capacity.

Reference 68 reports on the structure and adsorption properties of various calcium phosphate adjuvants. Rather than being strict Ca$_3$(PO$_4$)$_2$, the adjuvants were reported to be non-stoichiometric hydroxyapatite of formula Ca$_{10-x}$(HPO$_4$)$_x$(PO$_4$)$_{6-x}$(OH)$_{2-x}$ and a pH-dependent surface charge with a point of zero charge (PZC) of 5.5. The adjuvants can form needle-like particles having dimensions of approximately 10 nm×150 nm as well as irregularly shaped plates having diameters of approximately 20-30 nm.

Reference 69 discloses a reactive amorphous calcium phosphate, containing reactive vacant sites, the reactive sites having been obtained by removal of a carbonate pre-component of carbonated amorphous calcium phosphate by thermal decomposition of the pre-component into gaseous or vaporous by-products.

References 70 & 71 disclose a particulate calcium phosphate adjuvant ("CAP"), wherein the particle has a diameter in the range of 300-4000 nm (nanoparticle) and has a spherical shape and a smooth surface. Reference 72 discloses that these particles can be used for mucosal immunization.

Mucosal immunization is also disclosed in reference 73, where a method for vaccinating a mammal to cause an IgA antibody response uses particulate hydroxylated calcium phosphate of a size suitable for transport across epithelium.

Reference 74 discloses composite particles that are soluble in vivo and which comprise a particle of a polymeric substance having a calcium phosphate compound having a Ca/P ratio of about 1.0 to 2.0 coated on its surface.

Reference 75 discloses an injectable aqueous gel of calcium phosphate for adsorbing vaccines, wherein calcium and phosphate ions are combined in proportions such that the weight ratio Ca/P is from 1.62 to 1.85, and such that the settling time of the gel when containing 0.07 atom Ca per liter is between 1-20 mm in 10 minutes at 20° C.

The Ca to P molar ratio of calcium phosphate adjuvants can vary e.g. between 1.35 and 1.83 [see chapter 8 of ref. 67]. The adsorption properties of the adjuvant have been found to vary depending on the conditions used during precipitation e.g. slow mixing gave an adjuvant with lower adsorption capacity that an adjuvant formed by quick mixing.

The amount of calcium phosphate in a vaccine of the invention, measured as Ca$^{++}$, may be between 0.1 mg/ml and 10 mg/ml e.g. between 0.5-5 mg/ml, preferably 0.75-3 mg/ml, 0.9-1.5 mg/ml, or about 1 mg/ml.

The calcium phosphate adjuvant has the capacity to adsorb antigens. For a given antigen, at least 80% (e.g. ≥85%, ≥90%, ≥92.5%, ≥95%, ≥97.5%, ≥97.5%, ≥98%, ≥99%, ≥99.5%, etc.) by weight of the total amount of that antigen is adsorbed. As calcium phosphate adjuvants are insoluble, the degree of adsorption can conveniently be measured by a method involving centrifugation and then determination of the amount of antigen in one (or both) of the solid or soluble material. Unabsorbed antigen will remain in solution after centrifugation. For example, the adsorption capacity of calcium phosphate adjuvants was measured by this method in reference 76. Adsorption of diphtheria and tetanus toxoids to 1 mg of $Ca^{++}$ was incomplete when (a) diphtheria toxoid levels rose above 100 Lf and (b) tetanus toxoid levels rose above 25 Lf.

For adsorption, a calcium phosphate adjuvant is preferably used in the form of an aqueous suspension to which the influenza antigen(s) is/are added. The calcium salt can be diluted to the required concentration before addition of the antigen.

Microparticles

Microparticles have been described for use as adjuvants e.g. see references 77 & 78.

Preferred microparticles are made from biodegradable and non-toxic polymers. For instance, they may be made from a polymer selected from the group consisting of: a poly(α-hydroxy acid), a polyhydroxy butyric acid, a polycaprolactone, a polyorthoester, a polyanhydride, and a polycyanoacrylate. Copolymers of these polymers can also be used e.g. or a copolymer of D,L-lactide and caprolactone.

Preferred polymers are poly(α-hydroxy acids), more preferably those selected from the group consisting of poly(L-lactide), poly(D,L-lactide) and poly(D,L-lactide-co-glycolide). The most preferred polymers are poly(D,L-lactide-co-glycolide) polymers, referred to as 'PLG'. Preferred poly(D,L-lactide-co-glycolide) polymers are those having a lactide/glycolide molar ratio ranging from 25:75 to 75:25, more preferably 40:60 to 60:40 e.g. about 50:50. A 50:50 PLG polymer, containing 50% D,L-lactide and 50% glycolide, will provide a fast resorbing copolymer while 75:25 PLG degrades more slowly, and 85:15 and 90:10, even more slowly, due to the increased lactide component.

These polymers are available in a variety of molecular weights, and the appropriate molecular weight for a given antigen is readily determined by one of skill in the art. For polylactides, for example, a suitable molecular weight will be on the order of about 2000 to 5000. For PLG, suitable molecular weights will generally range from about 10,000 to about 200,000, preferably about 15,000 to about 150,000, and most preferably about 50,000 to about 100,000. A useful range is from 30,000 Daltons to 70,000 Daltons.

Microparticles can have a diameter in the range of ~100 nm to ~150 μm, more preferably ~200 nm to ~30 μm in diameter, and most preferably ~500 nm to ~10 μm in diameter. They will typically be substantially spherical.

Microparticles can be made in various ways. For example, double emulsion/solvent evaporation techniques are known, which involve the formation of a primary emulsion consisting of droplets of polymer solution, which is subsequently mixed with a continuous aqueous phase containing a particle stabilizer/surfactant. More particularly, a water-in-oil-in-water (w/o/w) solvent evaporation system can be used to form the microparticles, as described in reference 79. In this technique, the particular polymer is combined with an organic solvent, such as ethyl acetate, dimethylchloride (also called methylene chloride and dichloromethane), acetonitrile, acetone, chloroform, and the like. The polymer will be provided in about a 2-15%, more preferably about a 4 10% and most preferably, a 6% solution, in organic solvent. The polymer solution is emulsified using e.g. a homogenizer. The emulsion is then combined with a larger volume of an aqueous solution of an emulsion stabilizer such as polyvinyl alcohol (PVA) or polyvinyl pyrrolidone. The emulsion stabilizer is typically provided in about a 2-15% solution, more typically about a 4-10% solution. The mixture is then homogenized to produce a stable w/o/w double emulsion. Organic solvents are then evaporated. The formulation parameters can be manipulated to allow the preparation of small (<5 μm) and large (>30 μm) microparticles. For example, reduced agitation results in larger microparticles, as does an increase in internal phase volume. Particle size can be determined by routine methods.

As well as using double-emulsion techniques, single emulsion techniques can also be used. Microparticles can also be formed using spray-drying and coacervation, or by air-suspension coating techniques, such as pan coating and Wurster coating. Ionic gelation can also be used.

Following preparation, microparticles can be stored as they are, or can be freeze-dried for further use.

One method for adsorbing antigen onto prepared microparticles is as follows. Microparticles are rehydrated and dispersed to an essentially monomeric suspension of microparticles using dialyzable detergents. Useful detergents include, but are not limited to, any of the various N-methylglucamides (known as MEGAs), such as heptanoyl-N-methylglucamide (MEGA-7), octanoyl-N-methylglucamide (MEGA-8), nonanoyl-N-methylglucamide (MEGA-9), and decanoyl-N-methylglucamide (MEGA-10); cholic acid; sodium cholate; deoxycholic acid; sodium deoxycholate; taurocholic acid; sodium taurocholate; taurodeoxycholic acid; sodium taurodeoxycholate; 3[(3-cholamidopropyl)dimethylammonio]-1-propane-sulfonate (CHAPS); 3-[(3cholamidopropyl)dimethylammonio]-2-hydroxy-1-propane-sulfonate (CHAPSO); N-dodecyl-N,N-dimethyl-3-ammonio1-propane-sulfonate (ZWITTERGENT 3-12); N,N-bis-(3-Dgluconeamidopropyl)-deoxycholamide (DEOXY-BIGCHAP); Noctylglucoside; sucrose monolaurate; glycocholic acid/sodium glycocholate; laurosarcosine (sodium salt); glycodeoxycholic acid/sodium glycodeoxycholate. Generally, a ratio of about 0.0156:1 detergent to microparticle (w:w) will be used, more preferably about 0.625:1, even more preferably about 0.25:1 and most preferably about 1:1 to 2:1, detergent to microparticle (w:w).

The microparticle/detergent mixture is then physically ground, e.g., using a ceramic mortar and pestle, until a smooth slurry is formed. An appropriate aqueous buffer, such as phosphate buffered saline (PBS) or Tris buffered saline, is then added and the resulting mixture sonicated or homogenized until the microparticles are fully suspended. The antigen of interest is then added to the microparticle suspension and the system dialyzed to remove detergent. The polymer microparticles and detergent system are preferably chosen such that the antigen of interest will adsorb to the microparticle surface while still maintaining activity of the antigen. The resulting microparticles containing surface adsorbed antigens may be washed free of unbound antigen and stored as a suspension in an appropriate buffer formulation, or lyophilized with the appropriate excipients, as described further below.

Microparticles can optionally treated to have a negatively-charged surface (e.g. with SDS) or a positively-charged surface (e.g. with a cationic detergent, such as CTAB). Changes in surface characteristics can change the adsorption characteristics according to the antigen to be adsorbed.

The Immunopotentiator

Compositions of the invention include an immunopotentiator, and it has been found that the combination of an immunopotentiator with an insoluble particulate adjuvant gives a surprisingly effective immunogenic composition.

Preferred immunopotentiators are agonists of Toll-Like Receptors (TLR). For example, they may be agonists of one or more of the human TLR1, TLR2, TLR3, TLR4, TLR7, TLR8, and/or TLR9 proteins. Preferred agents are agonists of TLR7 (e.g. imidazoquinilones) and/or, more preferably, of TLR9 (e.g. CpG oligonucleotides). These immunopotentiators are useful for activating innate immunity pathways.

Typical immunopotentiators are organic compounds, and they are usually not polymers. They may have a molecular weight of less than 2 kDa e.g. <1800 Da, <1600 Da, <1400 Da, <1200 Da, <1000 Da, <800 Da, <600 Da, <500 Da, <400 Da, <300 Da, or <200 Da.

Suitable immunopotentiators include, but are not limited to:

An immunostimulatory oligonucleotide, such as one containing a CpG motif (a dinucleotide sequence containing an unmethylated cytosine linked by a phosphate bond to a guanosine), or a double-stranded RNA, or an oligonucleotide containing a palindromic sequence, or an oligonucleotide containing a poly(dG) sequence.

3-O-deacylated monophosphoryl lipid A ('3dMPL', also known as 'MPL™') [80-83].

An imidazoquinoline compound, such as Imiquimod ("R837") [84,85], Resiquimod ("R-848") [86], and their analogs; and salts thereof (e.g. the hydrochloride salts). Further details about immunostimulatory imidazoquinolines can be found in references 87 to 91.

A thiosemicarbazone compound, such as those disclosed in reference 92. Methods of formulating, manufacturing, and screening for active compounds are also described in reference 92.

A tryptanthrin compound, such as those disclosed in reference 93. Methods of formulating, manufacturing, and screening for active compounds are also described in reference 93.

A nucleoside analog, such as: (a) Isatorabine (ANA-245; 7-thia-8-oxoguanosine):

and prodrugs thereof; (b) ANA975; (c) ANA-025-1; (d) ANA380; (e) the compounds disclosed in references 94 to 96; (f) a compound having the formula:

wherein:
$R_1$ and $R_2$ are each independently H, halo, —$NR_aR_b$, —OH, $C_{1-6}$ alkoxy, substituted $C_{1-6}$ alkoxy, heterocyclyl, substituted heterocyclyl, $C_{6-10}$ aryl, substituted $C_{6-10}$ aryl, $C_{1-6}$ alkyl, or substituted $C_{1-6}$ alkyl;

$R_3$ is absent, H, $C_{1-6}$ alkyl, substituted $C_{1-6}$ alkyl, $C_{6-10}$ aryl, substituted $C_{6-10}$ aryl, heterocyclyl, or substituted heterocyclyl;

$R_4$ and $R_5$ are each independently H, halo, heterocyclyl, substituted heterocyclyl, —C(O)—$R_d$, $C_{1-6}$ alkyl, substituted $C_{1-6}$ alkyl, or bound together to form a 5 membered ring as in $R_{4-5}$:

the binding being achieved at the bonds indicated by a ～～

$X_1$ and $X_2$ are each independently N, C, O, or S;

$R_8$ is H, halo, —OH, $C_{1-6}$ alkyl, $C_{2-6}$ alkenyl, $C_{2-6}$ alkynyl, —OH, —$NR_aR_b$, —$(CH_2)_n$—O—$R_c$, —O—$(C_{1-6}$ alkyl), —$S(O)_pR_e$, or —C(O)—$R_d$;

$R_9$ is H, $C_{1-6}$ alkyl, substituted $C_{1-6}$ alkyl, heterocyclyl, substituted heterocyclyl or $R_{9a}$, wherein $R_{9a}$ is:

the binding being achieved at the bond indicated by a ～～

$R_{10}$ and $R_{11}$, are each independently H, halo, $C_{1-6}$ alkoxy, substituted $C_{1-6}$ alkoxy, —$NR_aR_b$, or —OH;

each $R_a$ and $R_b$ is independently H, $C_{1-6}$ alkyl, substituted $C_{1-6}$ alkyl, —$C(O)R_d$, $C_{6-10}$ aryl;

each $R_c$ is independently H, phosphate, diphosphate, triphosphate, $C_{1-6}$ alkyl, or substituted $C_{1-6}$ alkyl;

each $R_d$ is independently H, halo, $C_{1-6}$ alkyl, substituted $C_{1-6}$ alkyl, $C_{1-6}$ alkoxy, substituted $C_{1-6}$ alkoxy, —NH₂, —NH(C₁₋₆ alkyl), —NH(substituted C₁₋₆ alkyl), —N(C₁₋₆ alkyl)₂, —N(substituted C₁₋₆ alkyl)₂, C₆₋₁₀ aryl, or heterocyclyl;

each $R_e$ is independently H, $C_{1-6}$ alkyl, substituted $C_{1-6}$ alkyl, $C_{6-10}$ aryl, substituted $C_{6-10}$ aryl, heterocyclyl, or substituted heterocyclyl;

each $R_f$ is independently H, $C_{1-6}$ alkyl, substituted $C_{1-6}$ alkyl, —C(O)$R_d$, phosphate, diphosphate, or triphosphate;

each n is independently 0, 1, 2, or 3;

each p is independently 0, 1, or 2; or or (g) a pharmaceutically acceptable salt of any of (a) to (f), a tautomer of any of (a) to (f), or a pharmaceutically acceptable salt of the tautomer.

Loxoribine (7-allyl-8-oxoguanosine) [97].

A polyoxidonium polymer [98,99] or other N-oxidized polyethylene-piperazine derivative.

Compounds disclosed in reference 100.

A compound of formula I, II or III, or salts thereof:

as defined in reference 101, such as 'ER 803058', 'ER 803732', 'ER 804053', ER 804058', 'ER 804059', 'ER 804442', 'ER 804680', 'ER 804764', 'ER 804057' (structure shown below):

Or ER-803022 (structure shown below):

- An aminoalkyl glucosaminide phosphate derivative, such as RC-529 [102,103].
- A phosphazene, such as poly[di(carboxylatophenoxy)phosphazene] ("PCPP") as described, for example, in references 104 and 105.
- Compounds containing lipids linked to a phosphate-containing acyclic backbone, such as the TLR4 antagonist E5564 [106,107]:

- Muramyl peptides, such as N-acetylmuramyl-L-threonyl-D-isoglutamine ("thr-MDP"), N-acetyl-normuramyl-L-alanyl-D-isoglutamine (nor-MDP), N-acetylglucsaminyl-N-acetylmuramyl-L-Al-D-isoglu-L-Ala-dipalmitoxy propylamide ("DTP-DPP", or "Theramide™"), N-acetylmuramyl-L-alanyl-D-isoglutaminyl-L-alanine-2-(1'-2'dipalmitoyl-sn-glycero-3-hydroxyphosphoryloxy)-ethylamine ("MTP-PE").
- Compounds disclosed in reference 108, including: Acylpiperazine compounds, Indoledione compounds, Tetrahydraisoquinoline (THIQ) compounds, Benzocyclodione compounds, Aminoazavinyl compounds, Aminobenzimidazole quinolinone (ABIQ) compounds [109,110], Hydrapthalamide compounds, Benzophenone compounds, Isoxazole compounds, Sterol compounds, Quinazilinone compounds, Pyrrole compounds [111], Anthraquinone compounds, Quinoxaline compounds, Triazine compounds, Pyrazalopyrimidine compounds, and Benzazole compounds [112].
- Methyl inosine 5'-monophosphate ("MIMP") [113].
- A polyhydroxlated pyrrolizidine compound [114], such as one having formula:

where R is selected from the group comprising hydrogen, straight or branched, unsubstituted or substituted, saturated or unsaturated acyl, alkyl (e.g. cycloalkyl), alkenyl, alkynyl and aryl groups, or a pharmaceutically acceptable salt or derivative thereof. Examples include, but are not limited to: casuarine, casuarine-6-α-D-glucopyranose, 3-epi-casuarine, 7-epi-casuarine, 3,7-diepi-casuarine, etc.

Small molecule immunopotentiators (SMIPs) such as:
N2-methyl-1-(2-methylpropyl)-1H-imidazo[4,5-c]quinoline-2,4-diamine;
N2,N2-dimethyl-1-(2-methylpropyl)-1H-imidazo[4,5-c]quinoline-2,4-diamine;
N2-ethyl-N2-methyl-1-(2-methylpropyl)-1H-imidazo[4,5-c]quinoline-2,4-diamine;
N2-methyl-1-(2-methylpropyl)-N2-propyl-1H-imidazo[4,5-c]quinoline-2,4-diamine;
1-(2-methylpropyl)-N2-propyl-1H-imidazo[4,5-c]quinoline-2,4-diamine;
N2-butyl-1-(2-methylpropyl)-1H-imidazo[4,5-c]quinoline-2,4-diamine;
N2-butyl-N2-methyl-1-(2-methylpropyl)-1H-imidazo[4,5-c]quinoline-2,4-diamine;
N2-methyl-1-(2-methylpropyl)-N2-pentyl-1H-imidazo[4,5-c]quinoline-2,4-diamine;
N2-methyl-1-(2-methylpropyl)-N2-prop-2-enyl-1H-imidazo[4,5-c]quinoline-2,4-diamine;
1-(2-methylpropyl)-2-[(phenylmethyl)thio]-1H-imidazo[4,5-c]quinolin-4-amine;
1-(2-methylpropyl)-2-(propylthio)-1H-imidazo[4,5-c]quinolin-4-amine;
2-[[4-amino-1-(2-methylpropyl)-1H-imidazo[4,5-c]quinolin-2-yl](methyl)amino]ethanol;
2-[[4-amino-1-(2-methylpropyl)-1H-imidazo[4,5-c]quinolin-2-yl](methyl)amino]ethyl acetate;
4-amino-1-(2-methylpropyl)-1,3-dihydro-2H-imidazo[4,5-c]quinolin-2-one;
N2-butyl-1-(2-methylpropyl)-N4,N4-bis(phenylmethyl)-1H-imidazo[4,5-c]quinoline-2,4-diamine;
N2-butyl-N2-methyl-1-(2-methylpropyl)-N4,N4-bis(phenylmethyl)-1H-imidazo[4,5-c]quinoline-2,4-diamine;
N2-methyl-1-(2-methylpropyl)-N4,N4-bis(phenylmethyl)-1H-imidazo[4,5-c]quinoline-2,4-diamine;
N2,N2-dimethyl-1-(2-methylpropyl)-N4,N4-bis(phenylmethyl)-1H-imidazo[4,5-c]quinoline-2,4-diamine;
1-{4-amino-2-[methyl(propyl)amino]-1H-imidazo[4,5-c]quinolin-1-yl}-2-methylpropan-2-ol;
1-[4-amino-2-(propylamino)-1H-imidazo[4,5-c]quinolin-1-yl]-2-methylpropan-2-ol;
N4,N4-dibenzyl-1-(2-methoxy-2-methylpropyl)-N2-propyl-1H-imidazo[4,5-c]quinoline-2,4-diamine.

The immunopotentiator can be added to the composition at various stages during its production. For example, it may be within an antigen composition, and this mixture can then be added to an insoluble particulate adjuvant. As an alternative, it may be mixed with an insoluble particulate adjuvant, and this mixture can then be mixed with the antigen.

The immunopotentiator can optionally be conjugated to a separate agent, such as an antigen (e.g. CRM197). A general review of conjugation techniques for small molecules is provided in ref. 115. As an alternative, the immunopotentiators may be non-covalently associated with additional agents, such as by way of hydrophobic or ionic interactions.

Two preferred immunopotentiators are (a) immunostimulatory oligonucleotides and (b) 3dMPL.

Immunostimulatory Oligonucleotides

Immunostimulatory oligonucleotides can include nucleotide modifications/analogs such as phosphorothioate modifications and can be double-stranded or (except for dsRNA) single-stranded. References 116, 117 and 118 disclose possible analog substitutions e.g. replacement of guanosine with 2'-deoxy-7-deazaguanosine. The adjuvant effect of CpG oligonucleotides is further discussed in refs. 119-124. The CpG sequence may be directed to TLR9, such as the motif GTCGTT or TTCGTT [125]. The CpG sequence may be specific for inducing a Th1 immune response, such as a CpG-A ODN (oligodeoxynucleotide), or it may be more specific for inducing a B cell response, such a CpG-B ODN. CpG-A and CpG-B ODNs are discussed in refs. 126-128. Preferably, the CpG is a CpG-A ODN. Preferably, the CpG oligonucleotide is constructed so that the 5' end is accessible for receptor recognition. Optionally, two CpG oligonucleotide sequences may be attached at their 3' ends to form "immunomers". See, for example, references 125 & 129-131. A useful CpG adjuvant is CpG7909, also known as ProMune™ (Coley Pharmaceutical Group, Inc.).

As an alternative, or in addition, to using CpG sequences, TpG sequences can be used [132]. These oligonucleotides may be free from unmethylated CpG motifs.

The immunostimulatory oligonucleotide may be pyrimidine-rich. For example, it may comprise more than one consecutive thymidine nucleotide (e.g. TTTT, as disclosed in ref. 132), and/or it may have a nucleotide composition with >25% thymidine (e.g. >35%, >40%, >50%, >60%, >80%, etc.). For example, it may comprise more than one consecutive cytosine nucleotide (e.g. CCCC, as disclosed in ref. 132), and/or it may have a nucleotide composition with >25% cytosine (e.g. >35%, >40%, >50%, >60%, >80%, etc.). These oligonucleotides may be free from unmethylated CpG motifs.

Immunostimulatory oligonucleotides will typically comprise at least 20 nucleotides. They may comprise fewer than 100 nucleotides.

3dMPL

3dMPL (also known as 3 de-O-acylated monophosphoryl lipid A or 3-O-desacyl-4'-monophosphoryl lipid A) is an adjuvant in which position 3 of the reducing end glucosamine in monophosphoryl lipid A has been de-acylated. 3dMPL has been prepared from a heptoseless mutant of *Salmonella minnesota*, and is chemically similar to lipid A but lacks an acid-labile phosphoryl group and a base-labile acyl group. It activates cells of the monocyte/macrophage lineage and stimulates release of several cytokines. Preparation of 3dMPL was originally described in reference 133.

Combinations of 3dMPL and aluminum salts are already known e.g. with aluminum phosphate [134], or with aluminum hydroxide [135].

3dMPL can take the form of a mixture of related molecules, varying by their acylation (e.g. having 3, 4, 5 or 6 acyl chains, which may be of different lengths). The two glucosamine (also known as 2-deoxy-2-amino-glucose) monosaccharides are N-acylated at their 2-position carbons (i.e. at positions 2 and 2'), and there is also O-acylation at the 3' position. The group attached to carbon 2 has formula —NH—CO—CH$_2$—CR$^1$R$^1$. The group attached to carbon 2' has formula —NH—CO—CH$_2$—CR$^2$R$^{2'}$. The group attached to carbon 3' has formula —O—CO—CH$_2$—CR$^3$R$^{3'}$. A representative structure is:

Groups $R^1$, $R^2$ and $R^3$ are each independently —$(CH_2)_n$—$CH_3$. The value of n is preferably between 8 and 16, more preferably between 9 and 12, and is most preferably 10.

Groups $R^{1'}$, $R^{2'}$ and $R^{3'}$ can each independently be: (a) —H; (b) —OH; or (c) —O—CO—$R^4$, where $R^4$ is either —H or —$(CH_2)_m$—$CH_3$, wherein the value of m is preferably between 8 and 16, and is more preferably 10, 12 or 14. At the 2 position, m is preferably 14. At the 2' position, m is preferably 10. At the 3' position, m is preferably 12. Groups $R^{1'}$, $R^{2'}$ and $R^{3'}$ are thus preferably —O-acyl groups from dodecanoic acid, tetradecanoic acid or hexadecanoic acid.

When all of $R^{1'}$, $R^{2'}$ and $R^{3'}$ are —H then the 3dMPL has only 3 acyl chains (one on each of positions 2, 2' and 3'). When only two of $R^{1'}$, $R^{2'}$ and $R^{3'}$ are —H then the 3dMPL can have 4 acyl chains. When only one of $R^{1'}$, $R^{2'}$ and $R^{3'}$ is —H then the 3dMPL can have 5 acyl chains. When none of $R^{1'}$, $R^{2'}$ and $R^{3'}$ is —H then the 3dMPL can have 6 acyl chains. The 3dMPL adjuvant used according to the invention can be a mixture of these forms, with from 3 to 6 acyl chains, but it is preferred to include 3dMPL with 6 acyl chains in the mixture, and in particular to ensure that the hexaacyl chain form makes up at least 10% by weight of the total 3dMPL e.g. ≥20%, ≥30%, ≥40%, ≥50% or more. 3dMPL with 6 acyl chains has been found to be the most adjuvant-active form.

Thus the most preferred form of 3dMPL for inclusion in compositions of the invention is:

Where 3dMPL is used in the form of a mixture then references to amounts or concentrations of 3dMPL in compositions of the invention refer to the combined 3dMPL species in the mixture.

In aqueous conditions, 3dMPL can form micellar aggregates or particles with different sizes e.g. with a diameter<150 nm or >500 nm. Either or both of these can be used with the invention, and the better particles can be selected by routine assay. Smaller particles (e.g. small enough to give a clear aqueous suspension of 3dMPL) are preferred for use according to the invention because of their superior activity [136]. Preferred particles have a mean diameter less than 220 nm, more preferably less than 200 nm or less than 150 nm or less than 120 nm, and can even have a mean diameter less than 100 nm. In most cases, however, the mean diameter will not be lower than 50 nm. These particles are small enough to be suitable for filter sterilization. Particle diameter can be assessed by the routine technique of dynamic light scattering, which reveals a mean particle diameter. Where a particle is said to have a diameter of x nm, there will generally be a distribution of particles about this mean, but at least 50% by number (e.g. ≥60%, ≥70%, ≥80%, ≥90%, or more) of the particles will have a diameter within the range x±25%.

Substantially all of the 3dMPL is preferably located in the aqueous phase of the emulsion.

A typical amount of 3dMPL in a vaccine is 10-100 μg/dose e.g. about 25 μg or about 50 μg.

Pharmaceutical Compositions

Compositions of the invention are pharmaceutically acceptable. They may include components in addition to the antigen, adjuvant and immunopotentiator e.g. they will typically include one or more pharmaceutical carrier(s) and/or excipient(s). A thorough discussion of such components is available in reference 137.

The composition may include preservatives such as thiomersal or 2-phenoxyethanol. It is preferred, however, that the vaccine should be substantially free from (i.e. less than 5 μg/ml) mercurial material e.g. thiomersal-free [14,138]. Vaccines containing no mercury are more preferred. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [139], but keeping osmolality in this range is nevertheless preferred.

Compositions may include one or more buffers. Typical buffers include: a phosphate buffer; a Tris buffer; a borate buffer; a succinate buffer; a histidine buffer; or a citrate buffer. Buffers will typically be included in the 5-20 mM range.

The pH of a composition will generally be between 5.0 and 8.1, and more typically between 6.0 and 8.0 e.g. between 6.5 and 7.5, or between 7.0 and 7.8. A process of the invention may therefore include a step of adjusting the pH of the bulk vaccine prior to packaging.

The composition is preferably sterile. The composition is preferably non-pyrogenic e.g. containing <1 EU (endotoxin unit, a standard measure) per dose, and preferably <0.1 EU per dose. The composition is preferably gluten free.

The composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

The antigen, adjuvant and immunopotentiator in a composition will typically be in admixture. The compositions of the invention will typically be in aqueous form.

Compositions and kits are preferably stored at between 2° C. and 8° C. They should not be frozen. They should ideally be kept out of direct light.

Kits of the Invention

As mentioned above, compositions of the invention may be prepared extemporaneously, at the time of delivery. Thus the invention provides kits including the various components ready for mixing. The kit allows the adjuvant and the antigen to be kept separately until the time of use. The immunopotentiator may be included in one these two kit components, or may be part of a third kit component.

The components are physically separate from each other within the kit, and this separation can be achieved in various ways. For instance, the components may be in separate containers, such as vials. The contents of two vials can then be mixed e.g. by removing the contents of one vial and adding them to the other vial, or by separately removing the contents of both vials and mixing them in a third container.

In a preferred arrangement, one of the kit components is in a syringe and the other is in a container such as a vial. The syringe can be used (e.g. with a needle) to insert its contents into the second container for mixing, and the mixture can then be withdrawn into the syringe. The mixed contents of the syringe can then be administered to a patient, typically through a new sterile needle. Packing one component in a syringe eliminates the need for using a separate syringe for patient administration.

In another preferred arrangement, the two kit components are held together but separately in the same syringe e.g. a dual-chamber syringe, such as those disclosed in references 140-147 etc. When the syringe is actuated (e.g. during administration to a patient) then the contents of the two chambers are mixed. This arrangement avoids the need for a separate mixing step at the time of use.

The contents of the various kit components will generally all be in aqueous form. In some arrangements, a component (typically an antigen component rather than an adjuvant component) is in dry form (e.g. in a lyophilised form), with the other component being in aqueous form. The two components can be mixed in order to reactivate the dry component and give an aqueous composition for administration to a patient. A lyophilised component will typically be located within a vial rather than a syringe. Dried components may include stabilizers such as lactose, sucrose or mannitol, as well as mixtures thereof e.g. lactose/sucrose mixtures, sucrose/mannitol mixtures, etc. One possible arrangement uses an aqueous adjuvant component in a pre-filled syringe and a lyophilised antigen component in a vial.

Packaging of Compositions or Kit Components

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colorless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

Compositions of the invention are suitable for administration to human patients, and the invention provides a method of raising an immune response in a patient, comprising the step of administering a composition of the invention to the patient.

The invention also provides a kit or composition of the invention for use as a medicament.

The invention also provides the use of (i) an influenza virus antigen; (ii) an insoluble particulate adjuvant; and (iii) an immunopotentiator, in the manufacture of a medicament for raising an immune response in a patient.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [148]. Antibody responses are typically measured by hemagglutination inhibition, by microneutralisation, by single radial immunodiffusion (SRID), and/or by single radial hemolysis (SRH). These assay techniques are well known in the art.

Compositions of the invention can be administered in various ways. The most preferred immunisation route is by intramuscular injection (e.g. into the arm or leg), but other available routes include subcutaneous injection, intranasal [149-151], oral [152], intradermal [153,154], transcutaneous, transdermal [155], etc.

Vaccines prepared according to the invention may be used to treat both children and adults. Influenza vaccines are currently recommended for use in pediatric and adult immunisation, from the age of 6 months. Thus the patient may be less than 1 year old, 1-5 years old, 5-15 years old, 15-55 years old, or at least 55 years old. Preferred patients for receiving the vaccines are the elderly (e.g. ≥50 years old, ≥60 years old, preferably ≥65 years), the young (e.g. ≤5 years old), hospitalised patients, healthcare workers, armed service and military personnel, pregnant women, the chronically ill, immunodeficient patients, patients who have taken an antiviral compound (e.g. an oseltamivir or zanamivir compound, such as oseltamivir phosphate; see below) in the 7 days prior to receiving the vaccine, and people travelling abroad. The vaccines are not suitable solely for these groups, however, and may be used more generally in a population. For pandemic strains, administration to all age groups is preferred.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Preferred compositions of the invention satisfy 1, 2 or 3 of the CPMP criteria for efficacy. In adults (18-60 years), these criteria are: (1)≥70% seroprotection; (2)≥40% seroconversion; and/or (3) a GMT increase of ≥2.5-fold. In elderly (>60 years), these criteria are: (1)≥60% seroprotection; (2)≥30% seroconversion; and/or (3) a GMT increase of ≥2-fold. These criteria are based on open label studies with at least 50 patients.

Vaccines of the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3(1-ethylpropoxy)-1-cyclohexene-1-carboxylic acid or 5-(acetylamino)-4-[(aminoiminomethyl)-amino]-2,6-anhydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encapholopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

Where a cell substrate is used for reassortment or reverse genetics procedures, it is preferably one that has been approved for use in human vaccine production e.g. as in Ph Eur general chapter 5.2.3.

BRIEF DESCRIPTION OF DRAWINGS

FIG. 1 shows H1N1.

FIG. 2 shows H3N2.

FIG. 3 shows influenza B.

FIG. 5 shows GMTs (AU/ml) for IgG. The left bar in each pair shows IgG1; the right shows IgG2a.

MODES FOR CARRYING OUT THE INVENTION

Influenza virus strains Wyoming H3N2 (A), New-Caledonia H1N1 (A) and Jiangsu (B) were separately grown on MDCK cells. A trivalent surface glycoprotein vaccine was prepared and was used to immunize immune-naïve Balb/C mice at 0.1 µg HA per strain at days 0 and 28, intramuscularly. Animals were bled at day 42 and various antibody assays were performed with the blood: HI titers; anti-HA responses, measured by ELISA. IgG responses were classified as IgG1 or IgG2a.

Three insoluble particulate adjuvants were tested: (i) an aluminum hydroxide, used at 1 mg/ml and including a 5 mM histidine buffer; (ii) calcium phosphate, used at 1 mg/ml and including a 5 mM histidine buffer; or (iii) microparticles formed from poly(lactide co-glycolide) 50:50 co-polymer composition, intrinsic viscosity 0.4 ('PLG').

Two immunopotentiators were tested: (a) an immunostimulatory CpG ODN with a phosphorothioate backbone, at 10 µg/dose; and (b) R-848.

Thus there were 12 animal groups:

|  | (i) Al—H | (ii) Ca—P | (iii) PLG | No partic. adj. |
|---|---|---|---|---|
| No immunopot" | 1 | 2 | 3 | 10 |
| (a) CpG | 4 | 5 | 6 | 11 |
| (b) R-848 | 7 | 8 | 9 | 12 |

For the Al—H formulations, trivalent antigen was adsorbed to aluminium hydroxide at 1 mg/ml, 3 µg/ml antigen, 5 mM Histidine buffer pH 6.5 and 9 mg/ml Sodium Chloride at 4° C. overnight.

For the Ca—P formulations, a calcium phosphate suspension was homogenized at 15,000 rpm for 3 minutes using a 20-mm probe to reduce particle size. The antigens were then adsorbed to the homogenized suspension at 1 mg/ml Ca—P, 3 µg/ml antigen, in 5 mM Histidine buffer pH6.5 and 9 mg/ml Sodium Chloride overnight at 4° C.

PLG microparticles were prepared by a solvent evaporation method. Briefly, microparticles were prepared by homogenizing 10 ml of 6% w/v polymer solution in methylene chloride with 2.5 ml of phosphate-buffered saline (PBS) using a 10-mm probe. The water-in-oil emulsion thus formed was then added to 50 ml of distilled water containing DSS, and the mixture was homogenized at very high speed with a 20-mm probe for 5 minutes in an ice bath. This procedure resulted in the formation of a water-in-oil-in-water emulsion that was then stirred at 1000 rpm for 12 hours at room temperature. The methylene chloride was allowed to evaporate. The size distribution of the resulting microparticles was determined with a particle size analyzer. The zeta potential was measured with a Malvern Zeta analyzer. Antigen was adsorbed at a load of 0.03% w/w by incubating a suspension containing 100 mg of blank PLG microparticles with 30 µg trivalent influenza antigen. Concentrated Histidine buffer solution was added to a final concentration of 10 mM pH 6.2 in a 10 ml total volume. The suspension was allowed to mix on a lab rocker at 4° C. overnight. 1 mL was removed at that time to be used for the determination of adsorption efficiency. Aliquots containing 3.6 µg of trivalent antigen were placed into small glass vials and lyophilized at −50° C. and $90 \times 10^{-3}$ mBar, with mannitol and sucrose to affect a final concentration of 4.5% and 1.5% respectively upon reconstitution.

The efficiency of protein adsorption to the three adjuvants was determined as follows: 1 ml aliquot of PLG/FCC, Al—H/ FCC or Ca—P/FCC were removed following the overnight incubation step. After centrifugation the amount of unbound protein remaining in the supernatant was measured by gel filtration chromatography. Essentially, 100 µl of the supernatant was injected on a TSK3000SWXL with a Waters 2690/ 432 instrument. A linear calibration curve was established with trivalent antigen, and the amount of protein present in the supernatant was calculated. The total amount of unbound protein was then subtracted from the total amount of protein added initially and the difference was used to calculate the actual loading efficiency.

For antigen extraction from Al—H and Ca—P formulations, aliquots were centrifuged for 15-20 minutes at 5000 rpm. The supernatant from each sample was removed without disturbing the pellets. To displace the antigen, a desorbing buffer (0.25M $Na_2HPO_4$+0.15M EDTA) was added to each pellet and incubated for 2-3 hours at room temperature with gentle rocking. The extracted antigen was separated from the delivery system by centrifugation.

For antigen extraction from PLG microparticles, PBS was added with 0.05% Octyl-β-glucoside, incubated for 1-2 hours at room temperature under gentle rocking motion. The supernatant containing the extracted FCC antigens was separated from the pellet by centrifugation.

Antigen-specific antibodies were determined by ELISA. Titration of HA-specific IgG was performed on individual sera 2 weeks after the last immunization. Maxisorp 96-well flat-bottom plates were coated overnight at 27-30° C. with 0.2 µg/well with H1N1, H2N3 or B in phosphate-buffered saline pH 7.4 (PBS). The coated wells were blocked for 1 hour at room temperature with 300 µl of 3% PVP. The plates were washed with PBS pH 7.4, 0.1% BSA and 0.05% Tween-20, tapped and dried. Serum samples and serum standard were initially diluted 1:5,000-1:20,000 with the Dilution buffer (PBS pH 7.4, 1% BSA, 0.05% Tween-20), then transferred into coated-blocked plates in which the samples were serially diluted three-fold with the same buffer. Antigen-specific IgG was revealed with alkaline phosphatase-conjugated goat anti-mouse IgG. Antibody titers were expressed as the logarithm of the ELISA titers that gave an optical density (OD) higher than the mean plus five times the standard deviation (SD) of the average OD obtained in the preimmune sera. The titers were normalized with respect to the reference serum assayed in parallel.

Antibodies were also determined by a haemagglutination inhibition assay, carried out in V-shaped 96-well microtitre plates on individual sera, taken 2 weeks after the first immunization (post 1) and 2 weeks after the second immunization (post 2) Briefly, 25 µL of two-fold serially diluted samples are incubated with 25 µL strain-specific influenza antigen (whole virus, containing 4 haemagglutinating units) for 60 minutes at room temperature. A 0.5% v/v suspension of red blood cells obtained from adult cocks are added and the mixture is incubated for another 60 minutes. Reactions are followed through visual inspection: a red dot formation indicates a positive reaction (inhibition) and a diffuse patch of cells a negative reaction (haemagglutination). The titre is defined as the serum dilution in which the last complete agglutination inhibition occurs. The antibody concentration corresponds to the reciprocal value of the titre.

Figure 1:
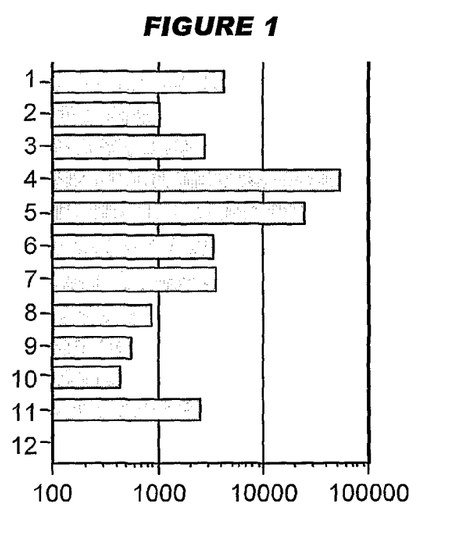
FIGS. 1 to 3 show the Log 10 serum antibody titers (ELISA) for mice immunized with different compositions.
Figure 2:
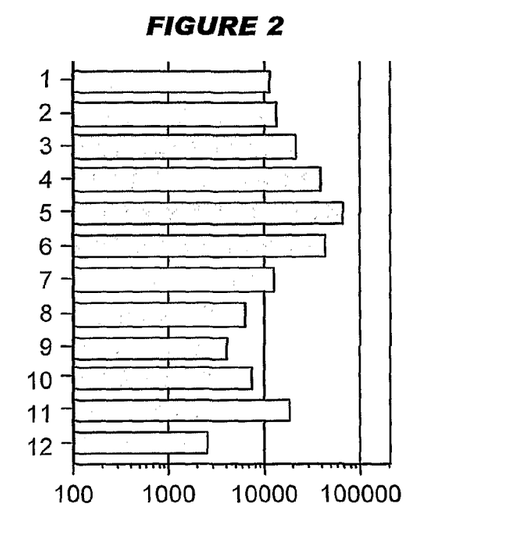
Figure 3:
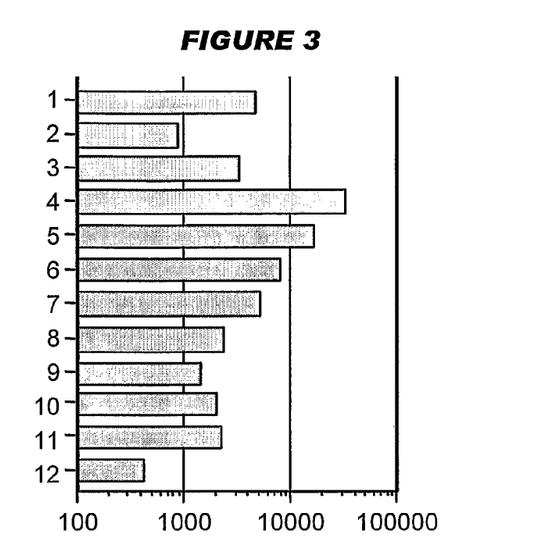

FIGS. 1 to 3 show anti-HA ELISA responses for the 12 groups. A comparison of groups 1 and 4 shows that addition of CpG to aluminum hydroxide increases HA titers. Similarly, CpG increases HA titers when added to the calcium phosphate adjuvant (groups 2 & 5) and to the PLG adjuvant (groups 3 & 6).

Figure 4:
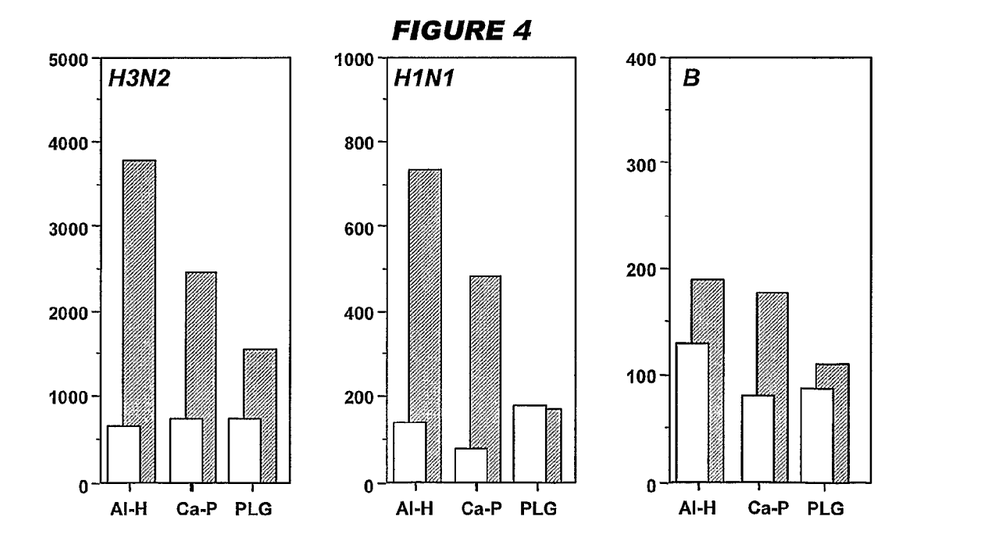
FIG. 4 shows HI titers. The foreground bars are groups 1 to 3, and the background bars are groups 4 to 6.

FIG. 4 shows HI titers for groups 1 to 6. The addition of CpG enhances HI titers.

Figure 5:
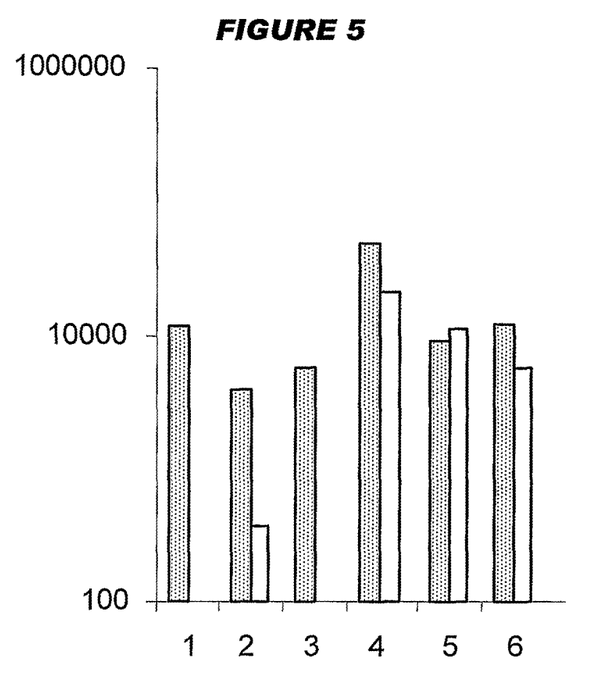

To see whether immune responses were of the TH1- or TH2-type, HA-specific IgG were sub-classified as IgG1 (TH2) or IgG2a (TH1). FIG. 5 shows the results of this analysis. The particulate antigens alone (groups 1, 2 & 3)

show very little IgG2a. When CpG is added, however, prominent IgG2a responses are seen (groups 4, 5 & 6), with IgG2a becoming dominant in group 5 (CpG+CaP). Thus the addition of an immunopotentiator, such as CpG, to the insoluble particulate adjuvants leads to a shift away from a TH2-type response and towards a TH1-type response. TH1-type responses have been reported to improve heterosubtypic immunity against influenza virus [9], and so known influenza vaccines containing insoluble particulate adjuvants can be improved by the addition of an immunopotentiator.

It will be understood that the invention has been described by way of example only and modifications may be made whilst remaining within the scope and spirit of the invention.

REFERENCES

The Contents of which are Hereby Incorporated by Reference

[1] Frey et al. (2003) *Vaccine* 21:4234-7.
[2] *Vaccines.* (eds. Plotkin & Orenstein). 4th edition, 2004, ISBN: 0-7216-9688-0.
[3] Espuelas et al. (2005) *Immonología* 24(2):208-23.
[4] U.S. Pat. No. 6,372,223.
[5] WO00/15251.
[6] WO01/22992.
[7] Hehme et al. (2004) *Virus Res.* 103(1-2):163-71.
[8] Coombes et al. (1998) *Biomaterials* 19(11-12):1073-81.
[9] Moran et al. (1999) *J Infect Dis* 180:579-85.
[10] WO96/37624.
[11] WO98/46262.
[12] WO02/28422.
[13] WO02/067983.
[14] WO02/097072.
[15] WO2005/113756.
[16] WO02/074336.
[17] WO01/21151.
[18] Huckriede et al. (2003) *Methods Enzymol* 373:74-91.
[19] Herlocher et al. (2004) *J Infect Dis* 190(9):1627-30.
[20] Le et al. (2005) *Nature* 437(7062):1108.
[21] World Health Organisation (2005) *Emerging Infectious Diseases* 11(10):1515-21.
[22] Hoffmann et al. (2002) *Vaccine* 20:3165-3170.
[23] Subbarao et al. (2003) *Virology* 305:192-200.
[24] Liu et al. (2003) *Virology* 314:580-590.
[25] Ozaki et al. (2004) *J. Virol.* 78:1851-1857.
[26] Webby et al. (2004) *Lancet* 363:1099-1103.
[27] WO00/60050.
[28] WO01/04333.
[29] U.S. Pat. No. 6,649,372.
[30] Neumann et al. (2005) *Proc Natl Acad Sci USA* 102:16825-9.
[31] WO2006/067211.
[32] WO01/83794.
[33] Hoffmann et al. (2000) *Virology* 267(2):310-7.
[34] WO97/37000.
[35] Brands et al. (1999) *Dev Biol Stand* 98:93-100.
[36] Halperin et al. (2002) *Vaccine* 20:1240-7.
[37] Tree et al. (2001) *Vaccine* 19:3444-50.
[38] Kistner et al. (1998) *Vaccine* 16:960-8.
[39] Kistner et al. (1999) *Dev Biol Stand* 98:101-110.
[40] Bruhl et al. (2000) *Vaccine* 19:1149-58.
[41] Pau et al. (2001) *Vaccine* 19:2716-21.
[42] http://www.atcc.org/
[43] http://locus.umdnj.edu/
[44] WO03/076601.
[45] WO2005/042728.
[46] WO03/043415.
[47] WO01/85938.
[48] WO2006/108846.
[49] EP-A-1260581 (WO01/64846).
[50] WO2006/071563.
[51] WO2005/113758.
[52] WO2006/027698.
[53] Lundblad (2001) *Biotechnology and Applied Biochemistry* 34:195-197.
[54] *Guidance for Industry: Bioanalytical Method Validation.* U.S. Department of Health and Human Services Food and Drug Administration Center for Drug Evaluation and Research (CDER) Center for Veterinary Medicine (CVM). May 2001.
[55] Ji et al. (2002) *Biotechniques.* 32:1162-7.
[56] Briggs (1991) *J Parenter Sci Technol.* 45:7-12.
[57] Lahijani et al. (1998) *Hum Gene Ther.* 9:1173-80.
[58] Lokteff et al. (2001) *Biologicals.* 29:123-32.
[59] EP-B-0870508.
[60] U.S. Pat. No. 5,948,410.
[61] International patent application entitled "CELL-DERIVED VIRAL VACCINES WITH LOW LEVELS OF RESIDUAL CELL DNA", filed 1 Nov. 2006 claiming priority U.S. 60/732,786.
[62] WO03/023021
[63] WO03/023025
[64] WO97/37001.
[65] Treanor et al. (1996) *J Infect Dis* 173:1467-70.
[66] Keitel et al. (1996) *Clin Diagn Lab Immunol* 3:507-10.
[67] *Vaccine Design: The Subunit and Adjuvant Approach* (eds. Powell & Newman) Plenum Press 1995 (ISBN 0-306-44867-X).
[68] Jiang et al. (2004) *Vaccine* 23:693-8.
[69] U.S. Pat. No. 5,676,976.
[70] WO00/46147.
[71] U.S. Pat. No. 6,355,271.
[72] WO03/051394.
[73] U.S. Pat. No. 5,443,832.
[74] U.S. Pat. No. 5,851,670.
[75] U.S. Pat. No. 4,016,252.
[76] Aggerbeck & Heron (1995) *Vaccine* 13:1360-5.
[77] WO98/33487.
[78] *Vaccine Adjuvants: Preparation Methods and Research Protocols* (Volume 42 of *Methods in Molecular Medicine* series). ISBN: 1-59259-083-7. Ed. O'Hagan.
[79] O'Hagan et al. (1993) *Vaccine* 11:965-9.
[80] Myers et al. (1990) pages 145-156 of *Cellular and molecular aspects of endotoxin reactions.*
[81] Ulrich (2000) Chapter 16 (pages 273-282) of reference 78.
[82] Johnson et al. (1999) *J Med Chem* 42:4640-9.
[83] Baldrick et al. (2002) *Regulatory Toxicol Pharmacol* 35:398-413.
[84] U.S. Pat. No. 4,680,338.
[85] U.S. Pat. No. 4,988,815.
[86] WO92/15582.
[87] Stanley (2002) *Clin Exp Dermatol* 27:571-577.
[88] Wu et al. (2004) *Antiviral Res.* 64(2):79-83.
[89] Vasilakos et al. (2000) *Cell Immunol.* 204(1):64-74.
[90] U.S. Pat. Nos. 4,689,338, 4,929,624, 5,238,944, 5,266,575, 5,268,376, 5,346,905, 5,352,784, 5,389,640, 5,395,937, 5,482,936, 5,494,916, 5,525,612, 6,083,505, 6,440,992, 6,627,640, 6,656,938, 6,660,735, 6,660,747, 6,664,260, 6,664,264, 6,664,265, 6,667,312, 6,670,372, 6,677,347, 6,677,348, 6,677,349, 6,683,088, 6,703,402, 6,743,920, 6,800,624, 6,809,203, 6,888,000 and 6,924,293.
[91] Jones (2003) *Curr Opin Investig Drugs* 4:214-218.

[92] WO2004/060308.
[93] WO2004/064759.
[94] U.S. Pat. No. 6,924,271.
[95] US2005/0070556.
[96] U.S. Pat. No. 5,658,731.
[97] U.S. Pat. No. 5,011,828.
[98] Dyakonova et al. (2004) *Int Immunopharmacol* 4(13): 1615-23.
[99] FR-2859633.
[100] PCT/US2005/022769.
[101] WO03/011223.
[102] Johnson et al. (1999) *Bioorg Med Chem Lett* 9:2273-2278.
[103] Evans et al. (2003) *Expert Rev Vaccines* 2:219-229.
[104] Andrianov et al. (1998) *Biomaterials* 19:109-115.
[105] Payne et al. (1998) *Adv Drug Delivery Review* 31:185-196.
[106] Wong et al. (2003) *J Clin Pharmacol* 43(7):735-42.
[107] US2005/0215517.
[108] WO2004/87153.
[109] U.S. Pat. No. 6,605,617.
[110] WO02/18383.
[111] WO2004/018455.
[112] WO03/082272.
[113] Signorelli & Hadden (2003) *Int Immunopharmacol* 3(8): 1177-86.
[114] WO2004/064715.
[115] Thompson et al. (2003) *Methods in Molecular Medicine* 94:255-266.
[116] Kandimalla et al. (2003) *Nucleic Acids Research* 31:2393-2400.
[117] WO02/26757.
[118] WO99/62923.
[119] Krieg (2003) *Nature Medicine* 9:831-835.
[120] McCluskie et al. (2002) *FEMS Immunology and Medical Microbiology* 32:179-185.
[121] WO98/40100.
[122] U.S. Pat. No. 6,207,646.
[123] U.S. Pat. No. 6,239,116.
[124] U.S. Pat. No. 6,429,199.
[125] Kandimalla et al. (2003) *Biochemical Society Transactions* 31 (part 3):654-658.
[126] Blackwell et al. (2003) *J Immunol* 170:4061-4068.
[127] Krieg (2002) *Trends Immunol* 23:64-65.
[128] WO01/95935.
[129] Kandimalla et al. (2003) *BBRC* 306:948-953.
[130] Bhagat et al. (2003) *BBRC* 300:853-861.
[131] WO03/035836.
[132] WO01/22972.
[133] UK patent application GB-A-2220211.
[134] WO96/26741.
[135] WO93/19780.
[136] WO 94/21292.
[137] Gennaro (2000) *Remington: The Science and Practice of Pharmacy.* 20th edition, ISBN: 0683306472.
[138] Banzhoff (2000) *Immunology Letters* 71:91-96.
[139] Nony et al. (2001) *Vaccine* 27:3645-51.
[140] WO2005/089837.
[141] U.S. Pat. No. 6,692,468.
[142] WO00/07647.
[143] WO99/17820.
[144] U.S. Pat. No. 5,971,953.
[145] U.S. Pat. No. 4,060,082.
[146] EP-A-0520618.
[147] WO98/01174.
[148] Potter & Oxford (1979) *Br Med Bull* 35: 69-75.
[149] Greenbaum et al. (2004) *Vaccine* 22:2566-77.
[150] Zurbriggen et al. (2003) *Expert Rev Vaccines* 2:295-304.
[151] Piascik (2003) *J Am Pharm Assoc* (Wash D.C.). 43:728-30.
[152] Mann et al. (2004) *Vaccine* 22:2425-9.
[153] Halperin et al. (1979) *Am J Public Health* 69:1247-50.
[154] Herbert et al. (1979) *J Infect Dis* 140:234-8.
[155] Chen et al. (2003) *Vaccine* 21:2830-6.

The invention claimed is:

1. An immunogenic composition comprising: (i) one or more inactivated influenza virus antigens, wherein at least one of the one or more influenza virus antigens is from a H1, H2, H3, H5, H7 or H9 influenza A virus subtype; (ii) an aluminum salt; and (iii) an oligonucleotide, wherein the oligonucleotide has a nucleotide composition with more than 40% cytosine.

2. The composition of claim 1, wherein at least one of the one or more influenza virus antigens is prepared from an influenza virus grown on cell culture.

3. The composition of claim 1, wherein at least one of the one or more influenza virus antigens is prepared from an influenza virus grown on eggs.

4. The composition of claim 1, wherein the composition is free from ovalbumin, ovomucoid and chicken DNA.

5. The composition of claim 2, wherein the composition contains less than 10 ng of cellular DNA from the cell culture host.

6. The composition of claim 2, wherein the composition contains less than 10 ng of DNA that is 100 nucleotides or longer.

7. The composition of claim 1, wherein the composition contains between 0.1 and 20 µg of haemagglutinin per viral strain.

8. The composition of claim 1, wherein the aluminum salt comprises an aluminum hydroxide.

9. The composition of claim 1, wherein the aluminum salt comprises an aluminum phosphate.

10. The composition of claim 1, wherein the composition comprises two or more inactivated influenza virus antigens, wherein at least two of the antigens are from different viral strains.

11. A kit comprising: (i) a first kit component comprising one or more inactivated influenza virus antigens; and (ii) a second kit component comprising an aluminum salt, wherein either (a) the first kit component or the second kit component includes an oligonucleotide, wherein the oligonucleotide has a nucleotide composition with more than 40% cytosine, or (b) the kit includes a third kit component comprising the oligonucleotide.

12. The kit of claim 11, wherein the first kit component comprises two or more inactivated influenza virus antigens, wherein at least two of the antigens are from different viral strains.

13. A method for preparing an immunogenic composition comprising the steps of combining: (i) one or more inactivated influenza virus antigens, wherein at least one of the one or more influenza virus antigens is from a H1, H2, H3, H5, H7 or H9 influenza A virus subtype; (ii) an aluminum salt; and (iii) an oligonucleotide, wherein the oligonucleotide has a nucleotide composition with more than 40% cytosine.

14. The method of claim 13, wherein (i) comprises two or more inactivated influenza virus antigens, wherein at least two of the antigens are from different viral strains.

* * * * *